United States Patent [19]

Kupchan et al.

[11] 4,013,664
[45] Mar. 22, 1977

[54] SYNTHESIS OF HERNANDALINE

[75] Inventors: S. Morris Kupchan, Charlottesville, Va.; Venkataraman Kameswaran, Levittown, Pa.

[73] Assignee: Research Corporation, New York, N.Y.

[22] Filed: June 20, 1973

[21] Appl. No.: 371,814

[52] U.S. Cl. .................. 260/288 D; 260/283 SY; 260/289 A; 260/289 C; 260/289 D
[51] Int. Cl.$^2$ .................................. C07D 217/04
[58] Field of Search ..... 260/289 A, 283 SY, 289 R, 260/289 C, 288 D

[56] References Cited

UNITED STATES PATENTS

| 3,131,191 | 4/1964 | Douglas et al. | 260/289 A |
| 3,376,305 | 4/1968 | Cava | 260/289 A |
| 3,717,643 | 2/1973 | Archer et al. | 260/289 A |
| 3,875,167 | 4/1975 | Kupchan et al. | 260/289 A |

OTHER PUBLICATIONS

Bentley, The Alkaloids, 1957, pp. 78–79.
von E. Schlittler et al.; Helvetica Chemica Acta., vol. 32, 1949, pp. 1880–1891.
Kerekes et al.; Chem. Abstr. vol. 73, 66768v, 1970.
Merck Index, 7th Edition, 1960, p. 1459 and p. 599.
Kupchan et al.; J. Am. Chem. Soc. vol. 95, pp. 2995–3000 (1973).
Kupchan et al.; J. Org. Chem. vol. 38 pp. 405–406 (1973).

Primary Examiner—Donald G. Daus
Assistant Examiner—Mary C. Vaughn
Attorney, Agent, or Firm—Behr & Woodbridge

[57] ABSTRACT

There is disclosed a novel and improved method of synthesizing aporphines utilizing the Pschorr cyclization of 1-(2'-aminobenzyl)-7 hydroxy-1,2,3,4-tetrahydroisoquinolines in place of the corresponding 7-methoxy compounds.

In the novel process of the present invention the amino group is diazotized and cyclized in the presence of copper powder.

10 Claims, No Drawings

SYNTHESIS OF HERNANDALINE

The invention described herein was made in the course of work under a grant or award from the Department of Health, Education and Welfare.

DESCRIPTION OF THE PRIOR ART

A total synthesis of the useful tumor inhibiting compound thalicarpine has been reported by Kupchan and Liepa (Chem. Commun. 599 (1971)). This novel synthesis includes, inter alia, a complete synthesis of a precursor, the known alkaloid hernandaline. In this synthesis, the yield determining step for the entire sequence to thalicarpine is, to all intents and purposes, the ring closing step leading to the aporphine nucleus. Heretofore, it has not been possible to raise the yield of this step above 15%. Thus if the yield of this step can be improved the total yield of the highly desirable thalicarpine can be correspondingly increased.

It has been demonstrated heretofore that the substitution of a 7-hydroxy group for a 7-methoxy group in the 1-(2'-substituted benzyl)-7-substituted-1,2,3,4-tetrahydroisoquinoline for the previously utilized 7-methoxy compound gave rise to improved yields. (Franck and Tietze, Angew Chem. Int. Ed. Engl. 6, 799 (1967), Spangler and Boop, Tetrahedron Lett., 4851 (1971)). Franck carries out a coupling in ferric chloride solution, that is to say, in a mildly acidic medium and also utilizes adjacent hydroxy groups which are not present in the system under consideration.

Spangler introduces a bromo group in the 2-position of the benzyl side-chain and carries his coupling in a basic medium under irradiation. These methods have not been found satisfactory in the synthetic sequence leading to hernandaline.

It is also well known in the art that copper will catalyze ring closure or other coupling reactions involving a diazo group.

However, it has been found that the use of a copper catalyst and a diazonium group in the 2-position of the benzyl side-chain will not enhance the yield where a methoxy group is present at the 7-position of the isoquinoline nucleus.

SUMMARY OF THE INVENTION

The novel process of the present invention may be summarized in the following flow chart.

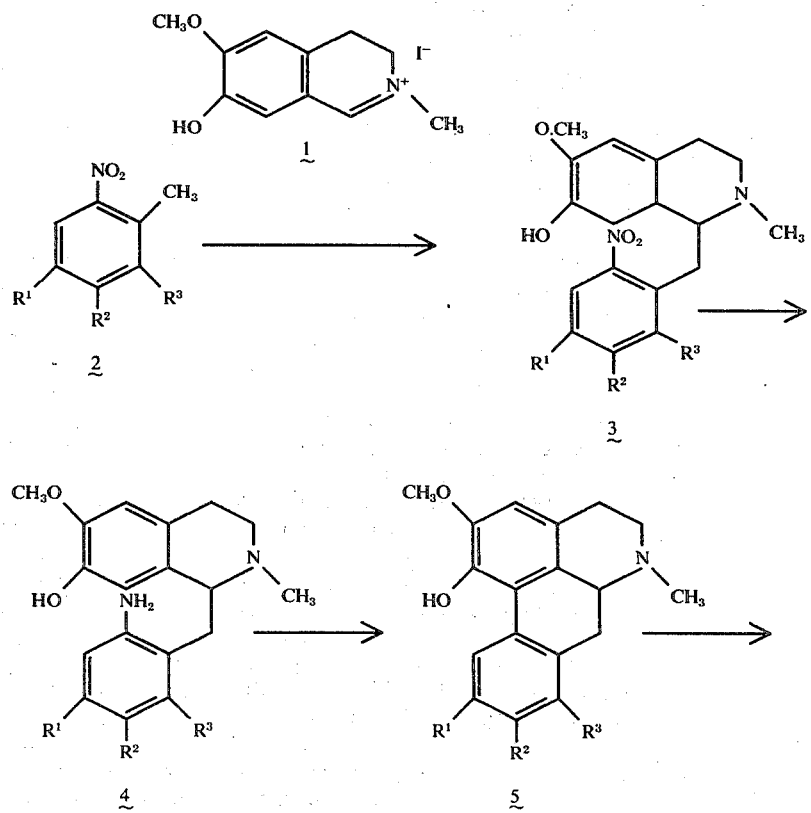

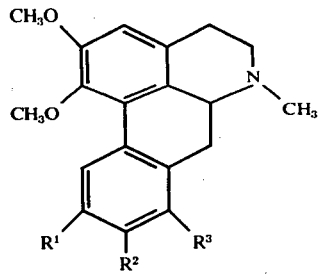

6 a. $R^1 = R^2 = R^3 = H$
b. $R^1 = R^2 = H; R^3 = OCH_3$
c. $R^1 = OCH_3; R^2 = Br; R^3 = H$
d. $R^1 = R^3 = H; R^2 = Cl$
e. $R^1 = OCH_3; R^2 = ODMP; R^3 = H$
   (ODMP: 3,4-dimethoxyphenoxy)
f. $R^1 = OCH_3, R^2 = H, R^3 = H$
g. $R^1 = R_2 = OCH_3, R_3 = H$ 6-Methoxy-7-hydroxy-3,4-dihydroisoquinolinium meth-halide is reacted with the appropriate o-nitro toluene in the presence of a strong, nonhydroxylic, base in a polar nonhydroxylic solvent to yield the corresponding 1-(2'-nitrobenzyl)-1,2,3,4-tetrahydroisoquinoline which is then reduced, suitably by catalytic hydrogenation to the corresponding amino phenol. Under certain circumstances discussed hereinbelow the reduction may be carried out by nascent hydrogen. The amino phenols are then diazotized in the conventional manner and treated with copper powder to induce cyclization to the appropriate aporphine. If desired, as for example in the synthesis of hernandaline, the 7-hydroxy group is then methylated.

DESCRIPTION OF THE PREFERRED EMBODIMENTS

The starting materials for the process of the present invention are a 6-methoxy-7-hydroxy 3,4-dihydroisoquinolinium meth-halide, for example, a meth-fluoride, meth-bromide or, preferably, the methiodide and a nitrotoluene, which may, if desired, be substituted. Among the suitable substituents are alkoxy groups such as methoxy, ethoxy, butoxy and the like, suitably having one to five carbon atoms, halo, such as fluoro, bromo, chloro, or iodo, or aroxy, suitably phenoxy, which may, if desired, bw substitued for example by further ether moieties such as 3,4-dimethoxy. The general method of the present invention permits positions 3 through 6 inclusive of the nitro toluene moiety to be substituted, however, for reasons of further synthesis, for example, in the synthesis of thalicarpine it is desirable to leave the 3-position unsubstituted.

In the process of reacting these two starting materials they are taken up in a polar, nonhydroxylic solvent, for example, N,N-dimethyl acetamide has been found especially suitable. There is then added a strong, nonhydroxylic base. An alkali metal alkoxide such as potassium t-butoxide or the like has been found suitable. There are utilized a slight excess, that is say, approximately 10 to 10% excess of the methiodide, and a substantial excess, that is to say, between 2 and 3 molecular equivalents of the base per mole of nitro toluene. The reaction mixture is worked up to yield the correspondng 1-(2'-nitrobenzyl)-1,2,3,4-tetrahydroisoquinoline which is then reduced.

The method of reduction utilized depends upon the substituents present on the nitro benzyl moiety. Where there are no substituents or where the substituents are alkoxy or aroxy catalytic hydrogenation in the presence of a suitable hydrogenation catalyst, for example, 5% palladium on charcoal may be employed. However, where halo substituents are present this mode of proceeding would lead to hydrogenolysis. Therefore, in these cases reduction is carried out by means of nascent hydrogen which may be generated by any suitable method. Zinc and sulfuric acid have been found especially suitable.

The thus produced amino phenols are then diazotized suitably by treatment with sodium nitrite in the presence of a mixture of aqueous sulfuric acid and acetic acid.

The diazotization is carried out at reduced temperatures, suitably from $-5°$ C to about $+5°$ C. The reaction mixture is agitated for a while, suitably for about 30 minutes, to ensure complete reaction and then the excess nitrous acid is destroyed by addition of solid sulfamic acid. An excess of finely divided copper suitably copper powder is added and the reaction mixture agitated at the same temperature until all the diazonium salt had disappeared (alkaine β-naphthol test). The copper powder is then removed by filtration, the filtrate made alkaline and the organic products extracted and worked up in the usual manner. The thus produced aporphine may be further purified by chromatography.

If desired, the thus produced aporphine may be taken up in a suitable reaction inert solvent for example, ethyl acetate, and treated with hydrobromic acid to yield the more readily crystallizable aporphine hydrobromide.

Where it is desired, as in the case of the synthesis of the precursor hernandaline, the hydroxy group at the 7 position of the isoquinoline nucleus is then alkylated, suitably methylated by treatment with an alkylating agent in the conventional manner. Where it is desired to produce a 7 methoxy group a solution of the aporphine in a suitable solvent, for example, methanol, is prepared and heated with an excess of diazo methane.

The foregoing general method of aporphine synthesis has been employed to produce several aporphines some of which are known and useful physiologically active compounds. Among the compounds produced by this method may be listed dl-nuciferine (6a), dl-thalicmidine (5g), and dl-glaucine (6g). Compound 6e may be subjected to formylation to produce hernandaline which in itself, as stated heretofore is a valuable precursor in the synthesis of thalicarpine.

Table I below shows the yields obtained for the various compounds produced by the process of the present invention as illustrated on the flow chart (supra). It should be noted that the yields for compounds 3, 4, and 5 represent the yield in the step from the previous compounds, whereas the yields for compounds 6 represent the combined yield for the cyclization and methylation step starting with compound 4. It will thus be seen that the procedure of the present invention is superior in yield to that which has been available heretofore.

TABLE I

| | Yields (Per Cent) | | | |
|---|---|---|---|---|
| | 3 | 4 | 5 | 6 |
| a | 90 | 87 | 44 | 48 |
| b | 88 | 93 | 45 | 40 |
| c | 95 | 83 | 43 | |
| d | 94 | 77 | 50 | 43 |
| e | 92 | 98 | 35 | 23* |
| f | | 81 | 46 | 36 |
| g | | 81 | 43 | 46 |

*(yield from 5e to 6e is 90% +)

Melting points were determined on a Thomas-Hoover capillary melting point apparatus. Ultraviolet spectra were determined in absolute ethanol solution on a Beckman DK-2A recording spectraphotometer. Infrared spectra were determined as KBr pellets on a Perkin-Elmer 257 recording spectrophotometer. Nmr spectra were recorded on a Varian HA-100 spectrometer in deuteriochloroform solution containing tetramethylsilane as internal standard. Mass spectra were determined on a Hitachi Perkin-Elmer RMU-6E spectrometer. Thin layer chromatography was carried out on silica get F-254 (Merck), and separated components were visualized by ultraviolet light and/or cerium sulfate (3%) in sulfuric acid (3N) spray followed by heating. Silica gel for column chromatography was 70–325 mesh or 70–230 mesh (Merck). All solutions were dried over anhydrous magnesium sulfate. Microanalyses were performed by Spang Microanalytical Laboratory, Ann Arbor, Mich.

EXAMPLE I 1-(2'-Nitrobenzyl)-2-methyl-6-methoxy-7-hydroxy-1,2,3,4-tetrahydroisoquinoline (3a)

Potassium-t-butoxide (0.9 g) was added, portionwise, over 20 min. to a stirred mixture of 2-nitrotoluene (0.5 g) and 7-hydroxy-6-methoxy-3,4-dihydroisoquinolinium methiodide (1.40 g), in N,N-dimethyl acetamide (20 ml) under an atmosphere of dry nitrogen. The reaction mixture was stirred at room temperature under nitrogen for 6 hours then diluted with water (200 ml) and extracted with ether (5 × 60 ml). The ether layers were extracted with 2N hydrochloric acid (4 × 50 ml), the acid layers were basified with aqueous ammonia and extracted with ether (5 × 50 ml). the combined organic extracts were washed with water (50 ml), dried, and evaporated to dryness to leave a brown oil (1.15 g). Chromatography of this material on silica gel (20 g) gave, on elution with chloroform (400 ml), the 1-(2'-nitrobenzyl)-2-methyl-6-methoxy-7-hydroxy-1,2,3,4-tetrahydroisoquinoline (3a) as a homogeneous (thin layer chromatography) foam (1.08 g, 90%); nmr τ 2.39 (m, 1H, C-11 $\underline{H}$), 2,68–3.12 (5H, aromatic $\underline{H}$), 4.73 (1H, O$\underline{H}$), 6.23 (s, 3H, OC$\underline{H}_3$), and 7.70 (s, 3H, NC$\underline{H}_3$).

The N-methiodide was prepared by reaction of free base 1-(2'-nitrobenzyl)-2-methyl-6-methoxy-7hydroxy-1,2,3,4-tetrahydroisoquinoline (3a) with methyl iodide in methanol overnight at room temperature. Crystallization of the crude product from methanol/ether gave pale yellow needles, mp. 218°–219°;

$\lambda_{Max}^{Kbr}$ 2.97 (O—H); $\lambda_{max}^{EtOh}$ (c) 282.5 nm (5460); mass spectrum m/e 342 ($M^+$—H—I), 192, 142, 120, 92, 91, 65, and 58.

Anal. Calcd. for $C_{19}H_{23}I N_2O_4$: C, 48.52; H, 4.93; N, 5.96; I, 26.98. Found: C, 48.67; H, 5.03; N, 6.03; I, 27.05.

EXAMPLE II 1-(2'-Aminobenzyl)-2-methyl-6-methoxy-7-hydroxy-1,2,3,4-tetrahydroisoquinoline Dihydrochloride (4a)

A solution of the 1-(2'-nitrobenzyl)-2-methyl-6-methoxy-7-hydroxy-1,2,3,4-tetrahydroisoquinoline (3a) (1.89 g) in absolute ethanol (200 ml) was hydrogenated at room temperature and atmospheric pressure over 5% palladium charcoal (0.18 g), until uptake of hydrogen ceased. The reaction mixture was filtered through celite and the filtrate evaporated to dryness to give a pale yellow foam (865 mg); mass spectrum m/e 296 ($M^+$ −1), 192, 187, 159, 85, 83, and 78. The crude product was dissolved in ethanol (200 ml) saturated with hydrogen chloride gas. The volume of solution was reduced to approximately 30 ml, and the solution was stored in the refrigerator overnight. Filtration gave the 1-(2'-aminobenzyl)-2-methyl-6-methoxy-7-hydroxy-1,2,3,4-tetrahydroisoquinoline dihydrochloride (4a) as colorless needles (2.028 g, 87%), mp 215°–217° (dec); $\lambda_{max}^{KBr}$ 2.96 $\mu$(O—H); $\lambda_{max}^{EtOH}$ (c) 231.5 (11,600) and 287.5 nm (5350); mass spectrum m/e 296 ($M^+$ − 1), 192, 187, and 158.

Anal. Calcd. for $C_{18}H_{24}N_2O_2Cl_2$: C, 58.23; H, 6.51; N, 7.54; Cl, 19.10. Found: C, 57.52; H, 6.71; N, 7.40; Cl, 18.87.

EXAMPLE III

1-Hydroxy-2-methoxyaporphine Hydrobromide (5a)

A solution of 1-(2'-aminobenzyl)-2-methyl-6-methoxy-7-hydroxy-1,2,3,4-tetrahydroisoquinoline dihydrochloride (4a) (270 mg) in 20% sulfuric acid (v/u, 4 ml) and glacial acetic acid (4 ml) at 0°–5° was treated, dropwise, with a solution of sodium nitrite (77 mg) in water (0.75 ml). After addition was complete, the mixture was stirred at ice bath temperature for 30 min. to complete diazotization. Sulfuric acid was added portionwise to destroy the excess nitrous acid, until a negative reaction was obtaned with potassium iodide-starch paper. Copper powder (380 mg) was added, and vigorous stirring at 0°–5° was continued for 1 hour. The mixture was diluted with water, basified with ammonium hydroxide, and extracted with chloroform (4 × 75 ml). The organic extract was washed with water (50 ml), dried and evaporated to dryness to give a brown gum (225 mg). This was dissolved in chloroform and rapidly passed through a column of silica gel (4 g), eluting with chloroform-methanol (97-3; 100 ml). Removal of solvents left a brown gum (216 mg) which was dissolved in ethyl acetate and treated dropwise with 48% hydrogen bromide with vigorous stirring. After thin layer chromatography indicated that no aporphine remained in solution, the mixture was stirred for 5 min. and the precipitate was collected by filtration, washed with ethyl/acetate and dried to give 1-hydroxy-2-methoxyaporphine hydrobromide (5a) (158 mg, 44%), mp 264°-266° (dec). Recrystallization from methanol gave the analytical sample, mp 267°-271° (dec); $\lambda_{max}^{KBr}$ 3.03 μ (O—H); $\lambda_{max}^{EtOH}$ (c) 270.5 (15,440) and 310.5 nm (5115); mass spectrum m/e 281 (m$^+$), 280, 266, 265, 264, 238, 223, and 206.

Anal. Calcd. for $C_{18}H_{20}BrNO_2$: C, 59.67; H, 5.57; N, 3.87; Br, 22.06. Found: C, 59.70; H, 5.55; N, 3.95; Br, 22.14

EXAMPLE IV

1,2-Dimethoxyaporphine Hydrobromide (Nuciferine Hydrobromide) (6a)

1-(2'-Aminobenzyl)-2-methyl-6-methoxy-7-hydroxy-1,2,3,4-tetrahydroisoquinoline Dihydrochloride (4a) (555 mg), dissolved in 20% sulfuric acid (6 ml) and glacial acetic acid (6 ml), was diazotised using sodium nitrite (116 mg) in water (1.1 ml). After addition of the copper powder (560 mg), the reaction mixture was stirred for 1 hour and treated as desscribed in Example III. The crude product was a brown gum (412 mg) which was dissolved in methanol (12 ml), and treated, at 3°-6°, with an ethereal solution of diazomethane, in aliquots over 6 days. After this time, thin layer chromatography, indicated no remaining hydroxyaporphine. Removal of solvents left a brown gum which was dissolved in chloroform and quickly filtered through a silica gel column (5 g), eluting with chloroform-methanol (97-3, 200 ml). Removal of solvent left a pale-brown gum (359 mg), which was treated as in Example III with 48% hydrobromic acid in ethyl acetate to give 1,2-dimethoxyaporphine hydrobromide (nuciferine hydrobromide) (6a) (262 mg, 48%), mp 253°-255° (dec); $\lambda_{max}^{EtOH}$ (c) 229 (23,660), 261 sh (14,370), 271 (18,225), and 309 nm sh (2805); mass spectrum m/e 295 (M$^+$), 294, 280, 264, 252, 237, and 221.

Anal. Calcd. for $C_{19}H_{22}BrNO_2$: C, 60.67; H, 5.91; N, 3.72; Br, 21.25. Found: C, 60.56; H, 5.90; N, 3.74; Br, 21.13.

EXAMPLE V

1-(3'-Chloro-6'-nitrobenzyl)-2-methyl-6-methoxy-7-hydroxy-1,2,3,4-tetrahydroisoquinoline (3d)

Potassium-t-butoxide (1.43 g) was added, portionwise, over 20 min. to a stirred mixture of 5-chloro-2-nitrotoluene (1 g) and 7-hydroxy-6-methoxy-3,4-dihydroisoquinolinium methiodide (2.23 g) in N,N-dimethylacetamide (40 ml) in an atmosphere of dry nitrogen. Stirring was continued under nitrogen for 6 hours. The reaction mixture was diluted with water and extracted with ether (5 × 100 ml). The organic layers were extracted with 2N-HCl (4 × 100 ml), basified with ammonium hydroxide and re-extracted with ether (5 × 100 ml). The combined ether layers were washed with water (2 × 100 ml), dried, and evaporated to dryness to leave a yellow oil (2.069 g). Chromatography of this material on silica gel (20 g), on elution with chloroform, gave the 1-(3'-chloro-6'-nitrobenzyl)-2-methyl-6-methoxy-7-hydroxy-1,2,3,4-tetrahydroisoquinoline (3d) as a homogeneous (thin layer chromatography) yellow oil which crystallized on standing (1.954 g, 94%), mp 123°-126°. Recrystallization from methanol-ether gave the analytical sample as bright yellow prisms, mp 127°-129°; $\lambda_{max}^{KBr}$ 3.17 and 3.24 μ (O-H), $\lambda_{max}^{EtOH}$ (c) 283 nm (7680); nmr τ 2.08-3.16 (4H, aromatic H̲), 5.08 (1H, OH̲), 4.13 (3H, s, O-CH̲$_3$), and 5.62 (3H, s, N—CH$_3$); mass spectrum m/e 363 (M$^+$ + 1), 361 (M$^+$ −1), 205, 192, 177, 148, 131, 119, 83, and 69.

Anal. Calcd. for $C_{18}H_{19}Cl\ N_2O_4$: C, 59.60; H, 5.28; N, 7.72. Found: C, 59.44; H, 5.36; N, 7.74.

EXAMPLE VI

1-(2'-Amino-5'-chloro)-2-methyl-6-methoxy-7-hydroxy-1,2,3,4-tetrahydroisoquinoline (4d)

4N Sulfuric acid (55 ml) was added, dropwise, to a stirred mixture of 1-(3'-chloro-6'-nitrobenzyl)-2-methyl-6-methoxy-7-hydroxy-1,2,3,4-tetrahydroisoquinoline (3d) and zinc dust (8.1 g) in methanol (30 ml) over approximately 45 min., while maintaining at atmosphere nitrogen over the reaction mixture. Stirring was continued for a further 2 hours the excess zinc dust was removed by filtration, and the filtrate was diluted with water and basified with ammonia. The resulting organic layers were washed repeatedly with water until no blue color was extracted. The chloroform layer was dried, decolorized with Draco charcoal, and evaporated to give the crude product as a pale greenish gum (1.84 g). Crystallization from ethanol gave colorless rosettes of 1-(2'-amino-5'-chloro)-2-methyl-6-methoxy-7-hydroxy-1,2,3,4-tetrahydroisoquinoline (4d) (1,385 g, 77%), mp 116°-118°. The analytical sample was recrystallized from ethanol, mp 118°-119°; $\lambda_{max}^{KBr}$ 2.90 and 2.98 μ (O—H and N—H); $\lambda_{max}^{EtOH}$ (c) 237 sh (11,700) and 289.5 nm (5810); nmr τ 3.06-3.64 (5H, aromatic H̲), 5.32 (3H, OH̲, NH̲$_2$), 6.22 (3H, s, O—CH̲$_3$), and 7.60 (3H, s, N—CH̲$_3$); mass spectrum m/e 331 (M$^+$ − 1), 300, 192, 177, and 148.

Anal. Calcd for $C_{18}H_{21}Cl\ N_2O_2$: C, 64.94; H, 6.37; N, 8.42; Cl, 10.65. Found: C, 64.74; H, 6.17; N, 8.45; Cl, 10.53.

EXAMPLE VII

9-Chloro-1-hydroxy-2-methoxyaporphine (5d)

1-(2'-Amino-5'-chloro)-2-methyl-6-methoxy-7-hydroxy-1,2,3,4-tetrahydroisoquinoline (4d) (332 mg), dissolved in 20% sulfuric acid (4 ml) and glacial acetic acid (4 ml), was diazotized, using sodium nitrite (77 mg) in water (0.75 ml) and reacted in accordance with Example III. After addition of copper powder (335 mg), the reaction mixture was stirred for 1 hour at ice-bath temperature and worked-up as usual. The crude product was a pale brown gum (307 mg) which crystallized from ether-methanol to give 9-chloro-1-hydroxy-2-methoxyaporphine (5d) was colorless crystals (140 mg, %), mp 155°-157°. Recrystallization from ether-methanol then from ether gave the analytical sample, mp 158.5°-159.5°, $\lambda_{max}^{KBr}$ 2.87 μ (O—H); $\lambda_{max}^{EtOH}$ (c) 236 sh (32,680), 276 (42,920), 288 sh (32,290), 313 (12,420), and 266.5 nm sh (33,479); nmr τ 1.78 (1H, d, J=9.5 Hz, C-11 H̲), 2.74-2.80 (2H, C-8, C-10 H̲), 3.53 (1H, s, C-3 H̲), 6.20 (3H, s, O—CH̲$_3$), and 7.52 (3H, s. N—CH̲$_3$); mass spectrum m/e 317 (M$^+$ + 2), 316 (M$^+$ +1), 315 (M$^+$), 314 (M$^+$ − 1), 300, 299, 298, and 272.

Anal. Calcd for $C_{18}H_{18}Cl\ NO_2$: C, 68.47; H, 5.74; N, 4.24; Cl, 11.23. Found: C, 68.19; H, 5.71; N, 4.47; Cl, 11.17.

EXAMPLE VIII

9-Chloro-1-hydroxy-2-methoxyaporphine Hydrochloride (5d)

The brown gum (256 mg) obtained as a crude product in accordance with Example VII was dissolved in ethanol and treated with ethanol (40 ml) saturated with hydrogen chloride gas. The volume of solution was reduced to approximately 8 ml, ether (4 ml) was added, and the mixture was stored overnight in the refrigerator. Filtration gave 9-chloro-1-hydroxy-2-methoxyaporphine hydrochloride (5d) as colorless crystals (176 mg, 50%), mp 244°–246° (dec). Recrystallization twice from methanolether gave the analytical sample, mp 246°–248° (dec); $\lambda_{max}^{KBr}$ 2.73–3.26 $\mu$ (broad, O-H and N-H); $\lambda_{max}^{EtOH}$ (c) 235 sh (28,490), 265.5 sh (28,080), 276 (37,589), 289 sh (27,250), and 313 nm (10,320); mass spectrum m/e 317, 316, 315 $M^+$ −HCl), 314 ($M^+$ − HCl-1), 300, 299, 298, and 272.

Anal. Calcd for $C_{18}H_{19}Cl_2NO_2 \cdot H_2O$: C, 58.38; H, 5.72; N, 3.78; Cl, 19.15. Found: C, 59.03; H, 5.57; N, 3.82; C., 18.91.

EXAMPLE IX

9-Chloro-1,2-dimethoxyaporphine Hydrochloride (6d)

The crude product from Pschorr cyclization (269 mg brown gum) carried out in accordance with the procedure of Example VII was dissolved in methanol (8 ml) and treated with excess of an ethereal solution of diazomethane at 3°–6° over 4 days. Thin layer chromatography indicated the methylation of hydroxyaporphine to be essentially complete at this time. Removal of solvents left a brown gum which was treated with ethanol (5ml) saturated with hydrogen chloride gas. The solvent was removed and the residue crystallized from ether-methanol to give 9-chloro-1,2-dimethoxyaporphine hydrochloride (6d) as colorless crystals (158 mg, 43%), mp 258°–259° (dec). Two recrystallizations from the same solvents gave the analytical sample, mp 259°–261° (dec); $\lambda_{max}^{KBr}$ 2.76–318 $\mu$ (broad, O—H and N—H); $\lambda_{max}^{EtOH}$ (c) 232 sh (16,060), 275.5 (19,160), and 315 nm sh (2010); mass spectrum m/e 331, 330, 329 ($M^+$ − HCl), 328 ($M^+$ − HCl-1), 314, 298, and 286.

Anal. Calcd for $C_{19}H_{21}Cl_2NO_2$: C, 62.29; H, 5.78; N, 3.82; Cl, 19.36. Found: C, 62.28 H, 5.26; N, 3.99; Cl, 19.19.

EXAMPLE X

1-(2'-Methoxy-6'-nitrobenzyl)-2-methyl-6-methoxy-7-hydroxy-1,2,3,4-tetrahydroisoquiniline (3b)

In accordance with the procedure of Example I 2-methoxy-6nitrotoluene (2 g) was allowed to react with 7-hydroxy-6-methoxy-3,4-dihydroisoquinolinium methiodide (4.8 g) and potassium-t-butoxide (3.1 g) in N,N-dimethylacetamide (100 ml). After the 6 hour reaction time, dilution with water caused most of the product, 1-(2'-methoxy-6'-nitrobenzyl)-2-methyl-6-methoxy-7-hydroxy-1,2,3,4-tetrahydroisoquinoline (3b), to precipitate as a bright yellow solid, which was collected, washed with water, and dried (3.46 g), mp 163°–165°. The usual acid-base treatment of the filtrate gave a further 0.286 g of 1-(2'-methoxy-6'-nitrobenzyl)-2-methyl-6-methoxy-7-hydroxy-1,2,3,4-tetrahydroisoquinoline (3b) (total yield 3.746 g, 88%). Recrystallization twice from methanol-ether gave bright yellow prisms, mp 167°–168°; $\lambda_{max}^{EtOH}$ (c) 284 (5640 and 324 nm (2390)); nmr τ 2.68–3.67 (5H, aromatic H), 4.58 (1H, O—H), 6.22 (3H, s, O—$CH_3$), and 7.77 (3H, s, O—$CH_3$); mass spectrum m/e 357 ($M^+$ − 1), 326, 324, 283, 192, and 177.

Anal. Calcd for $C_{19}H_{22}N_2O_5$: C, 63.38; H, 6.19; N, 7.82. Found: C, 63.80; H, 6.19; N, 7.87.

EXAMPLE XI

1-(2'-Amino-6'-methoxybenzyl)-2-methyl-6-methoxy-7-hydroxy-1,2,3,4-tetrahydroisoquinoline (4b)

A mixture of the 1-(2'-methoxy-6'-nitrobenzyl)-2-methyl-6-methoxy-7-hydroxy-1,2,3,4-tetrahydroisoquinoline (3b) (1 g) and 5% palladium-charcoal (0.2 g) in absolute ethanol (150 ml) was shaken with hydrogen at room temperature and atmospheric pressure overnight (19 hours). The mixture was filtered through celite, and the filtrate was evaporated to dryness to leave a transparent brown oil. This crystallized from methanol-ether to give 1-(2'-amino-6'-methoxybenzyl)-2-methyl-6-methoxy-7-hydroxy-1,2,3,4-tetrahydroisoquinoline (4b) (0.885 g, 93%), mp 158°–160°. Recrystallization from absolute ethanol gave feathery needles, mp 161°–162°; $\lambda_{max}^{KBr}$ 2.88 and 2.96 $\mu$ (OH and $NH_2$); $\lambda_{max}^{EtOH}$ (c) 285.5 nm (5480); nmr τ 3.02–3.87 (5H, aromatic H), 6.24 (6H, s, O—$CH_3$), and 7.66 (3H, s, N—$CH_3$); mass spectrum m/e 327 ($M^+$ − 1), 296, 205, 192, 177, and 148.

Anal. Calcd for $C_{19}H_{24}N_2O_3$: C, 69.47; H, 7.38; N, 8.53. Found: C, 69.47; H, 7.25; N, 8.56.

EXAMPLE XII

2,8-Dimethoxy-1-hydroxyaporphine Hydrobromide (5b)

A solution of 1-(2'-amino-6'-methoxybenzyl)-2-methyl-6-methoxy-7-hydroxy-1,2,3,4-tetrahydroisoquinoline (4b) (328 mg) in 20% sulfuric acid (4 ml) and glacial acetic acid (4 ml) was diazotized using sodium nitrite (77 mg) in water (0.75 ml), and subjected to Pschorr cyclization with copper powder (330 mg) as previously described in Example IV. The crude brown product thus obtained was streaked on 8 silica gel thin layer chromatography plates (20 × 20 cm, 0.5 nm thick) which were developed in methanol-chloroform (8:92). The aporphine band was cut off, eluted from the absorbent with methanol, filtered, and the filtrate evaporated to dryness. The residue was treated with chloroform (10 ml) and the mixture was filtered free of silica gel. Removal of the chloroform left a brown gum which was dissolved in ethyl acetate (5 ml) and treated, dropwise, with 48% hydrogen bromide as described in Example III, to give 2,8-dimethoxy-1-hydroxyaporphine hydrobromide (5b) (175 mg, 45%), mp 237°–239°. Two recrystallizations from methanol gave the analytical sample as off-white needles, mp 239°–241° (dec); $\lambda_{max}^{KBr}$ 2.86 $\mu$ (O—H); $\lambda_{max}^{EtOH}$ (c) 271.5 (15,640) and 310 nm sh (5600); mass spectrum m/e 311 ($M^+$ − HBr), 310 ($M^+$ − HBr-1), 296, 296, 280, 252, 250, 237, and 236.

Anal. Calcd for $C_{19}H_{22}BrNO_3$: C, 58.15; H, 5.65; N, 3.57. Found: C, 58.06; H, 5.53; N, 3.55.

EXAMPLE XIII

1,2,8-Trimethoxyaporphine (6b)

The crude product obtained in the cyclization step of Example XII (276 mg brown gum) was dissolved in methanol (5 ml) was treated with excess of an ethereal solution of diazomethane. Further aliquots of diazomethane solution was added regularly, but methylation appeared to proceed slowly. After 29 days the reaction was worked up as usual although thin layer chromatography indicated that a small amount of unreacted hydroxyaporphine still remained. Evaporaion of solvents left a pale yellow solid, which crystallized from ether-methanol to give 1,2,8-trimethoxyaporphine. (6b) as colorless crystals (62 mg), mp 184°–185°. Preparative thin layer chromatography of the mother liquors on silica gel, and crystallization from ether gave a further 67 mg of (total yield 129 mg, 40%). Recrystallization from ether-methanol, then from ether gave the analytical sample, mp 186.5°–187.5°; $\lambda_{max}^{EtOH}$ (c) 271 (21,035) and 297.5 nm sh (5870) nmr $\tau$ 2.03 (1H, d, J=9.5 Hz, C-11 $\underline{H}$), 2.62–3.53 (3H, aromatic $\underline{H}$), 6.19 (6H, s, O—C$\underline{H}_3$), 6.44 (3H, s, O—C$\underline{H}_3$), and 7.49 (3H, s, N—C$\underline{H}_3$); mass spectrum m/e 325 (M$^+$), 324 (M$^+$ − 1), 310, 294, 282, 267, 251, and 206.

Anal. Calcd for $C_{20}H_{23}NO_3$: C, 73,82; H, 7.12; N, 4.30. Found: C, 73.56; H, 7.03; N, 4.12.

EXAMPLE XIV 1-(2'-Nitro-4'-methoxy-5'-bromobenzyl)-2-methyl-6-methoxy-7-hydroxy-1,2,3,4-tetrahydroisoquinoline (3c)

Nitrogen was bubbled through N,N-dimethylacetamide (16 ml) for 10 min. 3-Bromo-4-methoxy-6-nitrotoluene (492 mg) was added and stirred for 5 min. followed by 2-methyl-6-methoxy-7-hydroxy-3,4-dihydroisoquinolinium iodide (766 mg). Potassium-t-butoxide (496 mg) was then added in 3 portions over a 10 min. period. The reaction mixture was stirred under nitrogen at room temperature for 4 hours and diluted with cold water (200 ml), and extracted with ether (3 × 100 ml). The ether portions were combined, washed with water (2 × 100 ml), saturated sodium chloride solution (1 × 50 ml) and dried magnesium sulfate. Evaporation of the solvent gave yellow crystalline solid 1-(2'-nitro-4'-methoxy-5'-bromobenzyl)-2-methyl-6-methoxy-7 -hydroxy-1,2,3,4-tetrahydroisoquinoline (3c) (828 mg, 95%), mp 146°–146.5°. An analytical sample was crystallized from absolute ethanol, mp 146.4°–146.7°; nmr $\delta$ (CDCl$_3$), 2.34 (s, 3H, NC$\underline{H}_3$), 3.84 and 3.92 (2S, 6H, 2OC$\underline{H}_3$), and 6.47, 6.55, 7.22 and 7.34 (4S, 4H, aromatic $\underline{H}$); mass spectrum m/e 192 (base peak,

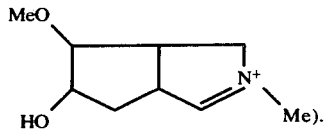

Anal. Calcd for $C_{19}H_{21}N_2O_5Br$ (437.29): C, 52.18; H, 4.84; N, 6.41; Br, 18.28. Found: Cm 52.02, H, 4.82; N, 6.50; Br, 18.21.

EXAMPLE XV 1-(2'-Amino-5'-bromo-4'-methoxybenzyl)-2-methyl-6-methoxy-7-hydroxy-1,2,3,4-tetrahydroisoquinoline Dihydrochloride (4c)

4N Sulfuric acid (17.4 ml) was added, dropwise over 25 min., to a stirred mixture of the 1-(2'-nitro-4'-methoxy-5'-bromobenzyl)-2-methyl-6-methoxy-7-hydroxy-1,2,3,4-tetrahydroisoquinoline (3c) (0.6 g) and zinc dust (2.56 g) in methanol (30 ml). Stirring was continued for 2 hours, the excess zinc was removed by filtration, and the filtrate was diluted with water and basified with ammonium hydroxide. The mixture was extracted with chloroform (5 × 60 ml), and the combined organic layers were washed with water (2 × 50 ml) and dried. Removal of solvent left a brown oil, which was treated with ethanol (8 ml) saturated with hydrogen chloride gas. Ether was added gradually, and the mixture was stored in the refrigerator overnight. Filtration gave the 1-(2'-amino-5'-bromo-4'-methoxybenzyl)-2-methyl-6-methoxy-7-hydroxy-1,2,3,4-tetrahydroisoquinoline dihydrochloride (4c) (0.546 g, 83%), mp 208°–211° (dec); $\lambda_{max}^{KBr}$ 2.74–3.19 $\mu$ (broad, O—H and N—H); $\lambda_{max}^{EtOH}$ (c) 238.5 sh (14,180) and 292 nm (6530); mass spectrum m/e 206, 192, 177, 87, and 60.

EXAMPLE XVI

9-Bromo-2,10-dimethoxy-1-hydroxyaporphine Hydrochloride (5c)

General procedure as described in Example III. 1-(2'-Amino-5'-bromo-4'-methoxybenzyl)-2-methyl-6-methoxy-7-hydroxy-1,2,3,4-tetrahydroisoquinoline dihydrochloride (4c) (448 mg) in 20% sulfuric acid (4 ml) and glacial acetic acid (4 ml) was diazotized using sodium nitrite (77 mg) in water (0.75 ml), and the subsequent Pschorr cyclization used copper powder (450 mg) in the usual manner. The crude product was a brown gum (353 mg) which was dissolved in chloroform and filtered through a short column of silica gel (3 g), eluting with chloroform-methanol (97:3, 200 ml). Removal of solvent left a brown gum which was treated with ethanol (6 ml) saturated with hydrogen chloride gas. Solvents were removed and the residue was stirred overnight with ether (30 ml). Filtration gave the crude aporphine hydrochloride as a pale brown solid (318 mg). Recrystallization from methanol gave 9-bromo-2,10-dimethoxy-1-hydroxyaporphine hydrochloride (5c) as a dull yellow crystalline solid (171 mg, 43%), mp 237°–240° (dec). Three recrystallizations from methanol pale yellow-greenish needles, mp 241°–243° (dec); $\lambda_{max}^{KBr}$ 2.75–3.30 $\mu$ (broad O—H and N—H); $\lambda_{max}^{EtOH}$ (c) 219 (39,415), 269.5 (13,710), 279.5 (16,970), 305 sh (13,195), and 311 nm (13,540); mass spectrum m/e 390, 389 (M$^+$ − HCl), 388 (M$^+$ − HCl-1), 387, 376, 374, 348, and 346.

Anal. Calcd for $C_{19}H_{21}BrCl\ N\ O_3.H_2O$: C, 51.37; H, 5.21; Br, 17.97; Cl, 7.97; N, 3.15. Found: C, 51.19; H, 5.04; Br, 17.92; Cl, 7.92; N, 3.16.

EXAMPLE XVII 1-(2'-Amino-4'-methoxybenzyl)-2-methyl-6-methoxy-7-hydroxy-1,2,3,4-tetrahydroisoquinoline Hydrobromide (4f)

A mixture of 1-(2'-nitro-4'-methoxy-5'-bromobenzyl)-2-methyl-6-methoxy-7-hydroxy-1,2,3,4-tetrahydroisoquinoline (3c) (850 mg) in absolute methanol (80 ml) containing palladium-charcoal catalyst (5%, 250 mg) was stirred under hydrogen until absorption ceased (approximately 6–8 hours). The catalyst was filtered, washed with methanol and the filtrate evaporated to give an oil which was crystallized from acetone to give white crystals of 1-(2'-amino-4'-methoxybenzyl)-2-methyl-6-methoxy-7-hydroxy-1,2,3,4-tetrahydroisoquinoline hydrobromide (4f) (735 mg, 81%), mp 136°–137.5°. An analytical sample was prepared by recrystallization from acetone, mp 137.5°–138°; nmr δ (CDCl$_3$), 2.05 (s, 6H, acetone C$\underline{H}_3$COC$\underline{H}_3$), 2.78 (s, 3H, NC$\underline{H}_3$), 3.88 and 3.92 (2s, 6H, 2OC$\underline{H}_3$), and 5.94–6.57 (CM, 5H, aromatic $\underline{H}$).

Anal. Calcd for $C_{22}H_{31}N_2O_4Br$ (467.40): C, 56.53; H, 6.69; N, 5.99; Br, 17.10. Found: C, 56.40; H, 6.74; N, 5.90; Br, 17.10.

EXAMPLE XVIII

1-Hydroxy-2,10-dimethoxyaporphine (5f)

A solution of 1-(2'-amino-4-methoxybenzyl)-2-methyl-6-methoxy-7-hydroxy-1,2,3,4-tetrahydroisoquinoline hydrobromide (4f) (407 mg) in aqueous sulfuric acid (20%, 8 ml) and glacial acetic acid (8 ml) at 0° C was diazotized by dropwise addition of a solution of sodium nitrite (70 mg) in water (1 ml) over a 10 min. period. The solution was stirred for 30 min. and excess nitrous acid was destroyed by addition of solid sulfamic acid. Copper powder (500 mg) was added and the reaction mixture was stirred at 0° C for 10 min. or until the diazonium salt had disappeared (alkaline β-naphthol test). The copper powder was removed by filtration and washed with water (50 ml). The combined filtrates were made alkaline with conc. ammonium hydroxide solution (30%) and extracted with chloroform (4 × 50 ml), washed with water (1 × 50 ml), dried magnesium sulfate and evaporated to give a residue. This was chromatographed on three 2mm silica gel plates and developed in 10% methanol-chloroform. The aporphine layer having $R_f$ .0131 was extracted with 20% methanolchloroform and evaporation of the solvent gave an oil (192 mg) which was crystallized from ethanol-ether to give a white solid 1-hydroxy-2,10-dimethoxyaporphine (5f) (125 mg, 47%), mp 193–194.5 (dec). An analytical sample was prepared by recrystallization from absolute ethanol, mp 194–194.8 (dec); $\lambda_{max}^{EtOH}$ (log ε), 305 (3.95), 274 (4.16), 265 (4.12) nm; nmr δ (CDCl$_3$) 2.52 (s, 3H, NC$\underline{H}_3$), 3.76 and 3.82 (2s, 6H, 2OMe), 6.56 (S, 1H, C-3$\underline{H}$), 6.76 (d of B part of an AB spectrum, J = 2.5Hz, $J_{AB}$ = 8Hz, 1H, C-9$\underline{H}$), 7.16 (A part of an AB spectrum, $J_{Ab}$ = 8Hz, 1H, C-8$\underline{H}$), and 8.02 (d. J = 25Hz, 1H, C-11$\underline{H}$); mass spectrum m/e 311 (M$^+$ − 1).

Anal. Calcd for $C_{19}H_{21}NO_3$ (311.37): C, 73.29; H, 6.80; N, 4.50. Found: C, 73.21; H, 6.89; N, 4.40.

EXAMPLE XIX

1-Hydroxy-2,10-dimethoxyaporphine hydrobromide (5f)

The diazotization and cyclization of 1-(2'-amino-4'-methoxybenzyl)-2-methyl-6-methoxy-7-hydroxy-1,2,3,4-tetrahydroisoquinoline hydrobromide (4f) was carried out as in Example XVIII, except that the only residue containing the crude aporphine was quickly passed through a short column of silica gal (10 g, backed in chloroform) and eluted with 5% methanol-chloroform. Evaporation of the organic solvents gave a residue which was dissolved in ethyl acetate and heated with a few drops of 48% hydrogen bromide to give 1-hydroxy-2,10-dimethoxyaporphine hydrobromide (5f) in 47% yield, mp 219–221.

Anal. Calcd for $C_{19}H_{22}NO_3Br$ (392.29): C, 58.17; H, 5.65; N, 3,57; Br, 20.37. Found: C, 57.97; H, 5.80; N, 3.49; Br, 20.39.

EXAMPLE XX 1,2,10-Trimethoxyaporphine hydrobromide (6f)

Crude 1-hydroxy-2,10-dimethoxyaporphine was prepared in accordance with Example XVIII. The residue obtained after removal of solvent from the chloroform extracts in the synthetic sequence was dissolved in absolute methanol (30 ml) and heated with excess of a solution of diazomethane in ether in small lots over a period of 3 days. Evaporation of solvents gave an oil which was dissolved in ethyl acetate (10 ml) and heated with hydrogen bromide (48%, 0.3 ml). The solid was filtered and crystallized from ethanol to give 1,2,10-trimethoxyaporphine hydrobromide (6f) (147 mg, 36%), mp 218°–222° (dec). An analytical sample was prepared by recrystallization from absolute ethanol, mp 223°–225° (dec); mass spectrum m/e 325 (M$^+$), 324.

Anal. Calcd for $C_{20}H_{24}NO_3Br$ (406.32): C, 59.12; H, 5.95; N, 3.45; Br, 19.46. Found: C, 58.84; H, 5.94; N, 3.37; Br, 19.46.

EXAMPLE XXI 1-(2'-Amino-4',5'-dimethoxybenzyl)-2-methyl-6-methoxy-7-hydroxy-1,2,3,4-tetrahydroisoquinoline Dihydrochloride (4g)

A mixture of 1-(2'-nitro-4',5'-dimethoxy-benzyl)-2-methyl-6-methoxy-7-benzyloxy-1,2,3,4-tetrahydroisoquinoline (1.50 g) in absolute methanol (100 ml) containing palladium-charcoal catalyst (5%, 0.45 g) was stirred under hydrogen until absorption ceased. The catalyst was filtered, washed with methanol and the filtrate evaporated to give an oil. Absolute ethanol (10 ml) was added followed by absolute ethanol saturated with hydrochloric acid gas (10 ml) to give 1-(2'-amino-4',5'-dimethoxybenzyl)-2-methyl-6-methoxy-7-hydroxy-1,2,3,4-tetrahydroisoquinoline dihydrochloride (4g) as a white solid (1.18 g, 81%), mp 177°–178°. An analytical sample was evaporated by recrystallization from ethanol, mp 177°–179°.

Anal. Calcd for $C_{20}H_{28}N_2O_4Cl_2$ (431.34): C, 55.69; H, 6.54; N, 6.49. Found: C, 55.72; H, 6.63; N, 6.51.

EXAMPLE XXII dl-Thalicmidine (5g)

A solution of 1-(2'-amino-4',5'-dimethoxybenzyl)-2-methyl-6-methoxy-7-hydroxy-1,2,3,4-tetrahydroisoquinoline (4g) (0.395 g) in aqueous sulfuric acid (20%, 8 ml) and glacial acetic acid (8 ml) at 0° C was diazotized by dropwise addition of a solution of sodium nitrite (70 mg) in water (1 ml). The solution was stirred for 30 min. and excess nitrous acid was destroyed by solid sulfamic acid. Copper powder (0.5 g) was added and the reaction mixture was stirred at 0° C for about 30 min. or until the diazonium salt had disappeared. The copper powder was filtered and washed with water (50 ml). The combined filtrates were made alkaline with conc. ammonium hydroxide solution (30%) and extracted with chloroform (4 × 30 ml), washed with water (50 ml), dried magnesium sulfate and evaporated to an oil. The oil was applied to 4 thin-layer plates (silica gel 8–254, 2 × 200 mm) and eluted with 10% methanol-chloroform. The aporphine band (dark on uv, $R_f$ 0.31) was collected and extracted with methanol-chloroform. The extract was evaporated to a residue, and extracting the residue with methylene chloride. Evaporation gave an oil which on addition of anhydrous ether gave dl-thalicmidine (5g) as a white solid (0.140 g, 43%), mp 190–192. The spectral properties (nmr, ms) were in agreement with the reported values for dl-thalicmidine.

EXAMPLE XXIII dl-Glaucine (6g)

The diazotization and cyclization of 1-(2'-amino-4',-5'-dimethoxybenzyl)-2-methyl-6-methoxy-7-hydroxy-1,2,3,4-tetrahydroisoquinoline dihydrochloride (4g) (0.431 g) was carried out as described in Example XXII. The oil obtained on evaporation of chloroform extract was dissolved in methanol (25 ml) and heated with excess of diazomethane periodically over 3 days while the reaction was kept in refrigerator. Evaporation of the solvents gave an oil which was dissolved in ethanol (10 ml) and heated with a solution of Picric acid (0.150 g) in ethanol (5ml) to give dl-glaucine (6g) as the monopicrate, as a yellow crystalline solid was collected. (0.270 g, 46%); mp 191°–192° (dec), mp 193°–194°.

EXAMPLE XXIV

1-[2'-Nitro-4'-methoxy-5'-(3'',4''-dimethoxy)phenoxybenzyl]-2-methyl-6-methoxy-7-hydroxy-1,2,3,4-tetrahydroisoquinoline (3e)

2,3',4'-Trimethoxy-5-methyl-4-nitrodiphenyl ether (2e) (6.38 g) was added to N,N-dimethyl acetamide (125 ml) under nitrogen, stirred for 5 min., and treated with 2 -methyl-6-methoxy-7-hydroxy-3,4-dihydroisoquinolinium iodide (1) (7.65 g). Potassium t-butoxide (4.39 g) was then added in small portions over 15 min. The reaction mixture was stirred under nitrogen at room temperature for 7 hours, diluted with cold water (600 ml), stirred for 10–15 min. and refrigerated overnight. The supernatant aqueous layer was decanted from the solid which was collected and washed with 1:1 methanol-ether (20 ml) followed by ether (100 ml) and sucked dry (9.40 g, 92%), to yield 1-[2'-nitro-4'-methoxy-5'-(3'', 4''-dimethoxy)phenoxybenzyl]-2-methyl-6-methoxy-7-hydroxy-1,2,3,4-tetrahydroisoquinoline (3e), mp 169°–171°. An analytical sample was crystallized from chloroform-methanol: mp 173°–174°; nmr δ 2.40 (3H, NCH$_3$), 3.85, 3.88, 3.92, and 3.98 (each 3H, 4 OCH$_3$), 6.37–7.60 (7H, ArH).

Anal. Calcd for C$_{27}$H$_{30}$N$_2$O$_8$: C, 63.52; H, 5.92; N, 5.49. Found: C, 63.46; H, 5.89; N, 5.34.

EXAMPLE XXV

1-[2'-Amino-4'-methoxy-5'-(3'',4''-dimethoxy)-phenoxybenzyl]-2-methyl-6-methoxy-7-hydroxy-1,2,3,4-tetrahydroisoquinoline (4e)

A mixture of 1-[2'-nitro-4'-methoxy-5'-(3'',4''-dimethoxy)phenoxybenzyl]-2-methyl-6-methoxy-7-hydroxy-1,2,3,4-tetrahydroisoquinoline (3e) (3.0 g) in absolute methanol (200 ml) containing palladium-charcoal catalyst (0.9 g, 5%) was stirred under hydrogen until absorption ceased. The catalyst was filtered, washed with 1:1 methanol-chloroform (50 ml), and the filtrate evaporated to give a brownish-yellow glass (2.7 g, 95%). The 1-[2'-amino-4'-methoxy-5'-(3'',4''-dimethoxy)phenoxybenzyl]-2-methyl-6-methoxy-7-hydroxy-1,2,3,4-tetrahydroisoquinoline (4e) was found to be unstable in solution and hence used as the crude material.

EXAMPLE XXVI

1-Hydroxy-2,10-dimethoxy-9-(3',4'-dimethoxy)-phenoxyaporphine (5e)

A solution of crude 1-[2'-amino-4'-methoxy-5'-(3'',-4''-dimethoxy)phenoxybenzyl]-2-methyl-6-methoxy-7-hydroxy-1,2,3,4-tetrahydroisoquinoline (4e) (7.65 g) in aqueous sulfuric acid (20%, 128 ml) and glacial acetic acid (128 ml) at 0° C was treated dropwise with a solution of sodium nitrite (1.12 g) in water (12 ml) over 10 min. The solution was stirred for 30 min. and excess nitrous acid was destroyed with sulfamic acid. Copper powder (8.00 g, Merck) was added and the reaction mixture was stirred at 0° C for 1 hour or until the diazonium salt had disappeared (alkaline β-naphthol test). The copper powder was filtered and washed with water (100 ml.) The filtrate was diluted to 300 ml with water, made alkaline with conc. ammonium hydroxide solution (30%) and extracted with chloroform (four 100 ml portions). The extracts were washed with water (2 × 100 ml), dried magnesium sulfate and evaporated to give a dark brown oil (8 g). This was applied to a silica gel column (Merck 0.2–0.05 mm, 400 g, packed in chloroform) and eluted with chloroform (ca. 3 l.) followed by 5% methanol-chloroform, which gave the crude 1-hydroxy-2,10-dimethoxy-9-(3',4'-dimethoxy)phenoxyaporphine (5e) as an off-white solid (3.54 g). Crystallization from ethanol-ether gave the pure 1-hydroxy-2,10-dimethoxy-9-(3',4'-dimethoxy)-phenoxyaporphine (5e) (2.62 g, 36%); mp 150.5°. An analytical sample was obtained by recrystallization from ethanol-ether: mp 150°–151°; $\lambda_{max}^{MeOH}$ (log ε), 278 (4.29), 302 (4.25), 268 sh (4.18) nm; nmr δ 2.52 (3H, N—CH$_3$), 3.84, 3.86, and 3.90 (3H, 3H, 6H, 4 OCH$_3$), 6.51–6.80 (5H, ArH), and 8.18 (1H, s, C-11 H).

Anal. Calcd. for C$_{27}$H$_{29}$NO$_6$: C, 69.95; H, 6.31; N, 3.02. Found: C, 69.68; H, 6.55; N, 3.20.

EXAMPLE XXVII

1,2,10-Trimethoxy-9-(3',4'-dimethoxy)phenoxyaporphine Hydrobromide (6e)

A mixture of 1-hydroxy-2,10-dimethoxy-9-(3',4'-dimethoxy)phenoxyaporphine (5e) (5.0 g) and methanol (100 ml) was treated with excess of diazomethane (ca. 8 g) in ether solution over a period of 3 days and the reaction was kept in the refrigerator with occasional swirling. The solution was evaporated to an oil which was dissolved in ethyl acetate (120 ml), treated with hydrogen bromide (48%, 1 ml) and stirred overnight. The white solid was collected, washed with ethyl acetate, and dried to give 1,2,10-trimethoxy-9-(3',4'-dimethoxy)phenoxyaporphine hydrobromide (6e) (5.42 g, 90%): mp 211°–214° (dec).

EXAMPLE XXVIII

(±)-Hernandaline

A mixture of 1,2,10-trimethoxy-9-(3',4'-dimethoxy)-phenoxyaporphine hydrobromide (6 e) (300 mg), N,N-dimethylformamide (1 g) and phosphorus oxychloride (1 g) in nitrobenzene (2 ml) was heated on a steam bath for 45 min., poured into aqueous phosphoric acid (2%, 100 ml), and extracted with ether (three 30 ml portions). The latter ether extracts were combined, evaporated, and the residue crystallized from aqueous ethanol to give (±)-hernandaline (174 mg, 65%): mp 148°–149.5°; nmr, ir and uv identical with hernandaline.

Anal. Calcd for $C_{29}H_{31}NO_7$: C, 68.91; H, 6.18; N, 2.77. Found: C, 68.79; H, 6.10; N, 2.78.

We claim:
1. A method of synthesizing an aporphine of the formula

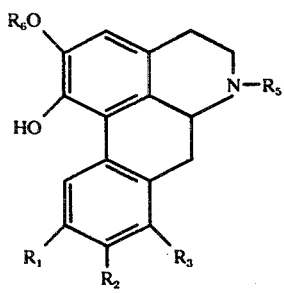

wherein
$R_1$ and $R_3$ are hydrogen, lower alkyl, lower alkoxy or phenoxy,
$R_2$ is hydrogen, halo, lower alkyl, lower alkoxy, or poly-lower alkoxy phenoxy,
$R_5$ is lower alkyl,
$R_6$ is hydrogen or lower alkyl,
wherein the prefix lower alk. signifies an alkyl moiety of 1–5 carbon atoms, which comprises the sequential steps of:
a. diazotizing a compound of the formula

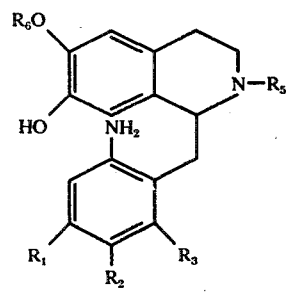

and
b. treating the thus produced diazonium salt with copper powder.
2. The process of claim 1 wherein
$R_1$ is H or methoxy,
$R_2$ is H, Cl, Br, methoxy or 3,4-dimethoxyphenoxy,
$R_3$ is H or methoxy,
$R_5$ is methyl,
$R_6$ is methyl.
3. The process of claim 2 wherein $R_1 = R_2 = R_3 = H$, $R_5 = R_6 =$ methyl.
4. The process of claim 2 wherein $R_1 = OCH_3$, $R_2 =$ 3,4-dimethoxyphenoxy, $R_3 = H$, $R_5 = R_6 =$ methyl.
5. The process of claim 2 wherein $R_1 = R_2 =$ methoxy, $R_3 = H$, $R_5 = R_6 =$ methyl.
6.

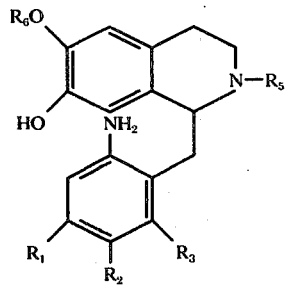

wherein $R_1$, $R_2$, $R_3$, $R_5$ and $R_6$ are defined in claim 1.
7. A compound of claim 6 wherein
$R_1$ is H or methoxy,
$R_2$ is H, Cl, Br, methoxy or 3,4-dimethoxyphenoxy,
$R_3$ is H or methoxy,
$R_5$ is methyl,
$R_6$ is methyl.
8. A compound of claim 6 wherein $R_1 = R_2 = R_3 = H$, $R_5 = R_6 =$ methyl.
9. A compound of claim 6 wherein $R_1 = OCH_3$, $R_2 =$ 3,4-dimethoxyphenoxy, $R_3 = H$, $R_5 = R_6 =$ methyl.
10. A process according to claim 1 wherein step (a) is carried out by treating the compound having the formula

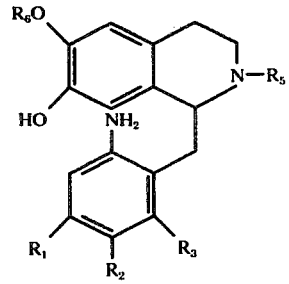

with nitrite ion in the presence of acid at a temperature of from about minus −5° C to about +5° C.

* * * * *